United States Patent
Teirstein et al.

(10) Patent No.: US 6,580,016 B2
(45) Date of Patent: Jun. 17, 2003

(54) ANIMAL MODEL FOR DETECTION OF VULNERABLE PLAQUES

(75) Inventors: Paul S. Teirstein, La Jolla, CA (US); Kenneth W. Carpenter, Del Mar, CA (US); Istvan Szinai, San Diego, CA (US); David A. Schwartz, Encinitas, CA (US)

(73) Assignee: Medivas, LLC, San Diego, CA (US)

( * ) Notice: Subject to any disclaimer, the term of this patent is extended or adjusted under 35 U.S.C. 154(b) by 107 days.

(21) Appl. No.: 09/760,182

(22) Filed: Jan. 12, 2001

(65) Prior Publication Data

US 2001/0018042 A1 Aug. 30, 2001

Related U.S. Application Data

(62) Division of application No. 09/453,668, filed on Dec. 3, 1999, now abandoned.
(60) Provisional application No. 60/111,084, filed on Dec. 4, 1998.

(51) Int. Cl.$^7$ ........................ A01K 67/00; A01K 67/033
(52) U.S. Cl. ............................................. 800/9; 424/9.1
(58) Field of Search ................................ 424/9.1, 1.11, 424/9.2; 800/9, 10, 11, 12

(56) References Cited

U.S. PATENT DOCUMENTS

| | | | |
|---|---|---|---|
| 4,752,141 A | 6/1988 | Sun et al. ................... 374/161 |
| 4,867,973 A | 9/1989 | Goers et al. .............. 424/85.91 |
| 5,217,456 A | 6/1993 | Narciso, Jr. ................... 606/15 |
| 5,275,594 A | 1/1994 | Baker et al. ................... 606/12 |
| 5,482,698 A | 1/1996 | Griffiths ..................... 424/141 |
| 5,591,772 A | 1/1997 | Lane et al. .................. 514/458 |
| 5,667,764 A | 9/1997 | Kopia et al. ................ 424/1.45 |
| 5,672,334 A | 9/1997 | Ranney ..................... 424/9.34 |
| 5,698,531 A | * 12/1997 | Nabel et al. ................... 514/44 |
| 5,843,403 A | 12/1998 | Dean ......................... 424/1.73 |
| 5,925,333 A | 7/1999 | Krieger et al. ............... 424/9.1 |

OTHER PUBLICATIONS

Iuliano et al (2000), Circulation, 101:1249–1254.*
Van Berkel et al (1981), FEBS Letters, 132 (No. 1):61–66.*
Baju et al. "Role of Inflammation in Coronary Plaque Disruption" *Circulation* 89:503–505,1994.

De Feyter et al. "Ischemia–Related Lesion Characteristics in Patients With Stable or Unstable Angina" *Circulation* 92:1408–1413, 1995.

Johnson et al., "The Molecular–weight Range of Mucosal-heparin Preparations" *Carbohydr Res* 51:119–127, 1976.

Ku et al., "Pulsatile Flow and Atherosclerosis in the Human Carotid Bifurcation" *Arteriosclerosis* 5/3:293–302,1985.

Mazzone et al., "Increased Expression of Neutrophil and Monocyte Adhesion Molecules in Unstable Coronary Artery Disease" *Circulation* 88:358–363, 1993.

van der Wal et al., "Site of Intimal rupture or Erosion of Thrombosed coronary Atherosclerotic Plaques Is Characterized by an Inflammatory Process Irrespective of the Dominant Plaque Morphology" *Circulation* 89:36–44, 1994.

* cited by examiner

*Primary Examiner*—Dameron L. Jones
(74) *Attorney, Agent, or Firm*—Gray Cary Ware & Freidenrich LLP; June M. Learn, J.D.

(57) ABSTRACT

The present invention provides in vivo methods for detection of vulnerable plaque in a subject in need thereof. In the invention method the subject is administered a diagnostic amount of a biologically compatible detectable lipid-avid agent, the detectable lipid-avid agent is allowed to penetrate arterial walls and attach to any lipid accumulations of oxidized LDL-cholesterol in arterial walls in the wall of an artery; unbound detectable lipid-avid agent is allowed to clear from the body by natural processes, and the presence of the detectable lipid-avid agent attached to the lipid accumulation in the wall of the artery is detected. Detection of bound lipid-avid agent indicates the presence of a vulnerable plaque and predicts a heightened risk of lethal heart attack or thrombus. The detectable lipid-avid agent is selected for its ability to penetrate arterial walls and bind with oxidized LDL-cholesterol in the lipid accumulation in a vulnerable plaque. Alternatively, macrophage-avid agents, for example a lipid-avid agent attached to a macrophage-specific antibody, can be used in the invention methods. The invention further includes methods for in vitro assays for detecting vulnerable plaque and a porcine animal model of vulnerable plaque useful for testing treatment modalities.

8 Claims, 4 Drawing Sheets

ANIMAL MODEL FOR DETECTION OF VULNERABLE PLAQUES

RELATED APPLICATION

This application is a divisional application of U.S. patent application Ser. No. 09/453,668, filed Dec. 3, 1999, now abandoned which claims priority from U.S. Provisional Application Serial No. 60/111,084, filed Dec. 4, 1998.

FIELD OF THE INVENTION

This invention relates to the medical diagnosis of arterial disease, and particularly to detection of vulnerable plaque by means of detection of lipid accumulations within the arterial system.

BACKGROUND OF THE INVENTION

Atherosclerotic coronary artery disease is the leading cause of death in industrialized countries. An atherosclerotic plaque is a thickened area in the wall of an artery. Typically, patients who have died of coronary disease may exhibit as many as several dozen atherosclerotic plaques; however, in most instances of myocardial infarction, cardiac arrest, or stroke, it is found that only one of these potential obstructions has, in fact, ruptured, fissured, or ulcerated. The rupture fissure, or ulcer causes a large thrombus (blood clot) to form on the inside of the artery, which may completely occlude the flow of blood through the artery, thereby injuring the heart or brain. A major prognostic and diagnostic dilemma for the cardiologist is how to predict which plaque is about to rupture.

Plaque, a thickening in the arterial vessel wall, results from the accumulation of cholesterol, proliferation of smooth muscle cells, secretion of a collagenous extracellular matrix by the cells, and accumulation of macrophages. Eventually, hemorrhage (bleeding), thrombosis (clotting), and calcification result. The consensus theory is that atherosclerotic plaque develops as a result of irritation or biochemical damage of the endothelial cells.

The endothelial cells which line the interior of the vessel prevent inappropriate formation of blood clots and inhibit contraction and proliferation of the underlying smooth muscle cells. Damage or dysfunction in endothelial cells is typically produced as a result of injury by cigarette smoke, diabetes, high serum cholesterol (especially oxidized low density lipoprotein), hemodynamic alterations (such as those found at vessel branch points), hypertension, some hormonal factors in the plasma (including Angiotensin II, norepinephrine),), certain viruses (herpes simplex, cytomegalovirus) and/or bacteria (e.g., Chlamydia), and other factors as yet unknown. As a result of these gradual injuries to the endothelial cells, an atherosclerotic plaque may grow slowly over many years. However, it is now well documented that if a plaque ruptures, it often grows abruptly by clot formation, occluding the blood vessel.

When plaque rupture develops, there is hemorrhage into the plaque through the fissure where the surface of the plaque meets the bloodstream. Blood coagulates (forms a thrombus) quickly upon contact with the matrix and lipid of the plaque. This blood clot may then grow to completely occlude the vessel, or it may remain only partially occlusive. In the latter case, the new clot quite commonly becomes incorporated into the wall of the plaque, creating a larger plaque.

Plagues at Risk of Rupturing

Given the enormous impact on public health of acute plaque disruption, much research has attempted to identify those factors which increase the likelihood of a plaque becoming destabilized. The term "vulnerable plaque" was coined to denote a lesion at risk of such an abrupt change.

Considerable evidence indicates that plaque rupture triggers 60% to 70% of fatal myocardial infarctions, and that monocyte-macrophages contribute to rupture by releasing metalloproteinases (e.g., collagenases, stromelysin), which can degrade and thereby weaken the overly fibrous cap (Van der Waal, et al., *Circulation* 89:36–44, 1994; Nikkari, et al., *Circulation* 92:1393–1398, 1995, Falk, et al., *Circulation* 92:2033–20335, 1995; Shad, et al., *Circulation* 244, 1995; Davies, et al., *Br Heart J* 53:363–373, 1985; Constantinides, *J Atheroscler Res* 6:1–17, 1966). In another 25% to 30% of fatal infarctions, the plaque does not rupture, but beneath the thrombus the endothelium is replaced by monocytes and inflammatory cells (Van der Waal, et al., *Circulation* 89:36–44, 1994; and Farb, et al., *Circulation* 92:1701–1709, 1995). These cells may both respond to and aggravate intimal injury, promoting thrombosis and vasoconstriction (Baju, et al., *Circulation* 89:503–505, 1994).

Unfortunately, neither plaque rupture nor plaque erosion is predictable by clinical means. Soluble markers, such as P-selectin, von Willebrand factor, Angiotensin-converting enzyme, C-reactive protein, D-dimer (Ikeda, et al., *Circulation* 92:1693–1696, 1995; Merlini, et al., *Circulation* 90:61–8, 1994; and Berk, et al., *Am J Cardiol* 65:168–172, 1990) and activated circulating inflammatory cells are found in patients with unstable angina pectoris, but it is not yet known whether these substances predict infarction or death (Mazzone, et al., *Circulation* 88:358–363, 1993). It is known, however, that the presence of such substances cannot be used to locate the involved lesion.

Angiograms may be useful for predicting a vulnerable plaque because low-shear regions opposite flow dividers are more likely to develop atherosclerosis (Ku, et al., *Arteriosclerosis* 5:292–302, 1985). However, most patients who develop acute myocardial infarction or sudden cardiac death have not had prior symptoms, much less an angiogram (Farb, et al., *Circulation* 92:1701–1709, 1995).

Certain angiographic data has revealed than an irregular plaque profile is a fairly specific, though insensitive, indicator of thrombosis (Kaski, et al., *Circulation* 92:2058–2065, 1955). Such plaques are likely to progress to complete occlusion, while others are equally likely to progress, but less often reach the point of complete occlusion (Aldeman, et al., *J Am Coll Cardiol* 22:1141–1154, 1993). Those that do abruptly progress to occlusion actually account for most myocardial infarctions (Ambrose, et al., *J Am Coll Cardiol* 12:56–62, 1988 and Little, et al., *Circulation* 78:1157–1166, 1988).

The size of the plaque occlusion is not necessarily determinative. Postmortem studies show that most occlusive thrombi are found over a ruptured or ulcerated plaque that is estimated to have produced a stenosis of less than 50% of the vessel diameter (Shah, et al., *Circulation* 244, 1995). Such stenoses are not likely to cause angina or result in a positive treadmill test. In fact, most patients who die of myocardial infarction do not have three-vessel disease or severe left ventricular dysfunction (Farb, et al., *Circulation* 92:1701–1709, 1995).

In the vast majority of plaques causing a stenosis less than or equal to 50% in vessel diameter, the surface outline is uniform, but the deep structure is highly variable and does not correlate directly with either the size of the plaque or the severity of the stenosis (Pasterkamp, et al., *Circulation* 91:1444–1449, 1995 and Mann and Davies *Circulation* 94:928–931, 1996).

In view of the dependence of vulnerability on the deep structure of the plaque, studies have been conducted to determine the ability to identify plaques likely to rupture using intracoronary ultrasound. It is known that (1) angiography tends to underestimate the extent of coronary atherosclerosis, (2) high echo-density usually indicates dense fibrous tissue, (3) low echo-density is a feature of hemorrhage, thrombosis, or cholesterol, and (4) shadowing indicates calcification (Yock, et al., *Cardio* 11–14, 1994 and McPherson, et al., *N Engl J Med* 316:304–309, 1987). However, recent studies indicate that intra-vascular ultrasound technology currently cannot discriminate between stable and unstable plaque (De Feyter, et al., *Circulation* 92:1408–1413, 1995).

The relation of the deep structure of the plaque to the rupture process is not completely understood, but it is known that the plaques most likely to rupture are those that have both a thick collagen cap (fibrous scar) and a point of physical weakness in the underlying structure. It is also known that plaques with inflamed surfaces or a high density of activated macrophages and a thin overlying cap are at risk of thrombosis (Van der Waal, et al., *Circulation* 89:36–44, 1994; Shah, et al., *Circulation* 244, 1995; Davies, et al., *Br Heart J* 53:363–373, 1985; Farb, et al., *Circulation* 92:1701–1709, 1995; and Van Damme, et al., *Cardiovasc Pathol* 3:9–17, 1994). Such points of physical weakness are thought to be located (as determined by modeling studies and pathologic analysis) at junctures where pools of cholesterol meet a more cellular and fibrous part of the plaque.

These junctures are also characterized by the presence of macrophages (inflammatory cells), which produce heat. Since macrophages and other inflammatory cells release enzymes capable of degrading the collagen and other components of the extracellular matrix, it is thought that they are crucial to the process of plaque rupture or fissuring.

Existing imaging modalities for identifying and treating vulnerable plaque are generally invasive and include coronary angiography, intravascular ultrasound, angioscopy, magnetic resonance imaging, and thermal imaging of plaque using infrared catheters.

For example, temperature sensing elements contained in catheters have been used for locating plaque on the theory that inflammatory processes and cell proliferation are exothermic processes. For example, U.S. Pat. No. 4,986,671 discloses a fiber optic probe with a single sensor formed by an elastomeric lens coated with a light reflective and temperature dependent material over which is coated a layer of material that is absorptive of infrared radiation. Such devices are used to determine characteristics of heat or heat transfer within a blood vessel for measuring such parameters as the pressure, flow and temperature of the blood in a blood vessel. As another example, U.S. Pat. No. 4,752,141 discloses a fiberoptic device for sensing temperature of the arterial wall upon contact. However, determination of temperature by contact requires preknowledge of the site where the catheter is to be placed (i.e., the locus whose temperature is to be determined).

Another type of prior art device is used for visualization of plaque features within a blood vessel, or for estimating the mass of a plaque. For example, U.S. Pat. No. 5,217,456 and U.S. Pat. No. 5,275,594, respectively, disclose the use of light that induces fluorescence in tissues, and of laser energy that stimulates fluorescence in non-calcified tissues. This type of device differentiates healthy tissue from atherosclerotic plaque, but is not reported to be useful for differentiating vulnerable plaque from other, less dangerous, forms of atherosclerotic plaque.

Efforts to develop methods and devices for the study and treatment of vulnerable plaque to date have been hampered by the lack of a reproducible large animal model of vulnerable plaque. Animals do not form plaque spontaneously. In some cases, the use of invasive technologies, such as prior art catheters, is expensive and, because such prior art devices must be threaded through the arterial tree, there is risk of causing damage to the intima that may itself trigger atherosclerotic processes. Accordingly, the need exists for new and better techniques for studying the characteristics of vulnerable plaque, for an animal model of vulnerable plaque, and for relatively inexpensive, non-invasive diagnostic methods for determining the presence of vulnerable plaque in the arteries of an individual.

SUMMARY OF THE INVENTION

In accordance with the present invention, there are provided in vivo methods for detection of vulnerable plaque(s) in a subject in need thereof. The invention diagnostic method comprises administering to the subject a diagnostically effective amount of a biologically compatible detectable lipid-avid agent so as to allow the detectable lipid-avid agent to associate with a lipid accumulation in the wall of an artery; and detecting in vivo the presence of the detectable lipid-avid agent attached to the lipid accumulation in the wall of the artery, wherein the detecting is evidence of the presence of a vulnerable plaque.

In another embodiment according to the present invention, there are provided in vivo methods for detection of vulnerable plaque(s) in a subject in need thereof using a macrophage-avid agent. In this embodiment, the invention diagnostic method comprises administering to the subject a diagnostically effective amount of a biologically compatible detectable macrophage-avid agent so as to allow the detectable macrophage-avid agent to associate with macrophages at a lipid accumulation in the wall of an artery; and detecting in vivo the presence of the detectable macrophage-avid agent attached to the macrophages at the lipid accumulation in the wall of the artery, wherein the detecting is evidence of the presence of a vulnerable plaque. Preferably the macrophage-avid agent comprises a lipid-avid agent attached to a macrophage specific antibody, or fragment thereof.

The invention diagnostic methods are useful for determining those individuals with a heightened probability of rupture of a vulnerable plaque with consequent formation of a thrombus in an artery. Thus, the invention methods are used for determining those individuals with a heightened probability of heart attack or stroke, especially of a fatal or near fatal heart attack or stroke. In addition, since pools of lipids in arterial walls are often associated with sites of inflammation and/or infection, including the gathering of macrophages and giant cells, the invention methods are useful for detecting sites of inflammation and/or infection in arterial walls associated with such pools of lipids.

In another embodiment according to the present invention, there are provided method(s) for obtaining an animal model of a vulnerable plaque, said method comprising:

locally depositing a plaque-forming amount of a lipid containing oxidized LDL into one or more blood vessel walls of a live pig while minimizing thrombogenesis so as to form one or more lipid accumulations in the vessel walls, and allowing the bodily processes of the live pig to react to the lipid accumulations to form one or more structures found in a human vulnerable plaque. One or more arterial structures in the live pig characteristic of a human vulnerable plaque will generally form within about 28 days to about 3 months from the date of lipid deposit The porcine model of a human vulnerable plaque is a useful animal model for studying the characteristics of human vulnerable plaques in the laboratory for the purpose of developing therapeutic methods of treating such vulnerable plaques.

In another embodiment according to the present invention, there are provided in vitro methods for detection of vulnerable plaque(s) in an arterial section. The invention in vitro diagnostic method comprises administering to the arterial section a diagnostically effective amount of a biologically compatible detectable lipid-avid agent so as to allow at least a portion of the detectable lipid-avid agent to attach to a lipid accumulation in the wall of the arterial section, and detecting the presence of the detectable lipid-avid agent attached to the lipid accumulation in the wall of the arterial section, wherein the detecting is evidence of the presence of a vulnerable plaque in the arterial section. Such methods are useful for studying the characteristics of vulnerable plaques in the laboratory for the purpose of developing therapeutic methods of treating such vulnerable plaques.

Accordingly, it is an object of the present invention to provide effective methods for identifying specific arterial sites at risk for arterial restenosis after angioplasty or atheroectomy.

It is a further object of the present invention to provide effective methods for identifying specific arterial sites associated with lipid pools having, or at risk of forming, sites of inflammation.

It is a further object of the present invention to provide effective methods for detecting transplant vasculopathy.

It is a further object of the present invention to provide methods for identifying vulnerable plaques not characterized by temperature higher than the temperature of surrounding healthy arterial walls, due to areas of extensive scarring, lipid pools where there is no cellular infiltration by macrophages, or areas of hemorrhage and thrombosis which have yet to be colonized by inflammatory cells.

It is a further object of the present invention to provide a reliable animal model of vulnerable plaques that will be useful for study of vulnerable plaques in humans and for development of therapeutic treatments for such plaques.

DETAILED DESCRIPTION OF THE INVENTION

The present invention is based upon the discovery that certain lipid-avid agents, when injected into the blood stream, pass through arterial walls and tend to accumulate in the lipid pools that characterize vulnerable plaques. Such lipid pools contain cholesterol and low density lipoproteins, particularly oxidized LDL-cholesterol, with which the lipid-avid agents bind in the lipid pools. By attaching a detectable label to such a lipid-avid agent or using a detectable lipid-avid agent and administering the detectable lipid-avid agent to a subject or to a section of arterial wall, it is possible to determine the presence, location, and extent of lipid pools in arterial walls that are indicative of vulnerable plaques, or associated with sites of inflammation, using known imaging techniques.

Accordingly, the present invention provides in vivo methods for detection of vulnerable plaque in a subject in need thereof. The invention method comprises administering to the subject a diagnostically effective amount of a detectable biologically compatible lipid-avid agent so as to allow the detectable lipid-avid agent to attach to a lipid accumulation in the wall of an artery; and detecting the presence of the detectable lipid-avid agent attached to the lipid accumulation in the wall of the artery, wherein the detecting is evidence of the presence of a vulnerable plaque. In one embodiment, the detectable lipid-avid agent is a lipid-avid agent having a detectable label attached thereto, for example, by covalent bond or chelation.

In an alternative embodiment, the present invention provides in vivo methods for detection of sites of infection associated with lipid pools in arterial walls in a subject in need thereof. In this embodiment, the invention method comprises administering to the subject a diagnostically effective amount of a detectable biologically compatible lipid-avid agent so as to allow the detectable lipid-avid agent to attach to a lipid accumulation in the wall of an artery; and detecting the presence of the detectable lipid-avid agent attached to the lipid accumulation in the wall of the artery, wherein the detecting is evidence of conditions conducive to the presence of a site of inflammation.

As used herein, the term "detectable lipid-avid agent" encompasses both lipid avid agents that are detectable in themselves, and lipid-avid agents that are made detectable by attachment thereto of a biologically compatible detectable label as disclosed herein.

The detectable lipid-avid agents of the invention are characterized by the property that they will penetrate readily through the walls of blood vessels. Upon administration to a subject, the invention detectable lipid-avid agent penetrates the walls of blood vessels throughout the circulatory system. A diagnostic amount of the lipid-avid agent may be administered as a single bolus injection or infusion, or several injections or infusions may be administered over several hours or days. A portion of the detectable lipid-avid agent that penetrates through the walls of blood vessels will contact the lipid accumulation(s) of any vulnerable plaques that may be present in the subject and become bound to oxidized LDL-cholesterol in such lipid accumulation(s) therein. The portion of the detectable lipid-avid agent that does not become bound to oxidized LDL-cholesterol in lipid accumulations in vulnerable plaque(s) will substantially metabolize and clear from the body of the subject over time by natural processes, e.g., by excretion as endogenous or natural carbohydrate-like compounds or derivatives. To determine whether any vulnerable plaques are present in the subject, the body of the subject is scanned using a scanning technique suitable to detection of the particular detectable lipid-avid agent used. The lipid-avid agent used in practice of the invention diagnostic methods is selected for its ability to penetrate the plaque and/or vessel wall and bind to oxidized LDL-cholesterol in the lipid accumulation in a vulnerable plaque.

Examples of lipid-avid agents that can be used in the practice of the invention methods include low molecular weight heparin, unfractionated heparin, and other types of lipid-avid polyanions, such as dextran sulfate, synthetic or semi-synthetic oligo or polysaccharides, glycosaminoglycans, natural polysaccharides, and the like. Generally, the lipid avid agent has a molecular weight in the range from about 3,000 to about 60,000, for example, from about 3,000 to about 8,000; however glycoproteins conjugates have a molecular weight in the range 10,000–150,000; for example heparin has a molecular weight in the range of 3,000 to about 40,000.

Heparin is highly lipophilic, non-toxic, and is known to bind with affinity to oxidized-LDL-cholesterol. This fact has been utilized for many years in the approach to drug resistant hypercholesterolemia of heparin induced LDL precipitation. As a result of these studies, intravenous and intramuscular dosing of heparin is well known.

Heparin consists of sulfated single chain glycoaminoglycans of variable length. Low molecular weight heparins are a group of derivatives of unfractionated heparin whose molecular weights have been well characterized by E. A. Johnson et al., *Carbohydr Res* 51:119–27, 1976, which is incorporated herein by reference in its entirety. Although widely used in Europe, the only low molecular weight heparin currently available in the United States is enoxaprin™ (Lovenox, Rhone-Poulenc Rorer). Other types of lipid-avid polyanions with chemical properties similar to those of heparin, such as dextran sulfate, dextran sulfate, synthetic or semi-synthetic oligo or polysaccharides, glycosaminoglycans, natural polysaccharides, and the like, can also be used as the lipid-avid agent in practice of the invention method. Generally the lipid avid agent has a molecular weight in the range having an upper limit from about 15,000 to about 60,000 and a lower limit from about 3,000 to about 8,000.

The portion of the detectable or detectably labeled lipid-avid agent administered to a subject that accumulates in and/or binds to lipid accumulations in vulnerable plaques or sites of inflammation therein becomes trapped in the arterial wall and will remain there for a considerable period of time, for example, up to several months. Therefore, procedures to detect the bound detectable lipid-avid agent are generally not performed until the unbound portion of the detectable lipid-avid agent (the portion that does not become trapped in lipid accumulations) has had a chance to sufficiently clear from the subject (e.g., from arterial walls). Upon clearance of the unbound portion of the detectable lipid-avid agent from the subject, the vulnerable plaque or site of inflammation can be distinguished from other portions of the arterial wall. The detecting can be performed no sooner than about 2 hours after the administering and for as long as several months after the administering of the detectable lipid-avid agent. Generally, however, detecting is performed from about 2 hours to about four weeks after the administering of the detectable lipid-avid agent to the subject.

Because the detectable lipid-avid agent remains trapped in lipid pools in vulnerable plaque over a long duration, it is also possible to repeat the detecting without the need to readminister the lipid-avid agent, for example, at spaced intervals of hours, days, or weeks, to monitor a subject over an extended period of time and thereby gauge the growth of a vulnerable plaque or inflammation associated therewith, and/or to determine the success of any therapeutic regimen undertaken for a subject.

The detectable lipid-avid agent is administered in a "diagnostically effective amount." An effective amount is the quantity of a detectable lipid-avid agent necessary to aid in in vivo or in vitro detection of one or more vulnerable plaques, or sites of inflammation associated therewith, located in the subject or arterial section under investigation. Amounts effective for diagnostic use will, of course, depend on a number of factors, such as the size of the subject or arterial section to be investigated, the affinity of the detectable lipid-avid agent for the lipids in the lipid pool(s) in vulnerable plaque, the location of the site under investigation, as well as the route of administration. Generally, however, since the pools of lipids in vulnerable plaques are small, usually in the size range from about 0.1 ml to about 5 ml, a diagnostically effective amount of the detectable lipid-avid agent used in practice of the invention method is generally in the range from about 0.1 cubic centimeter to about 200 cubic centimeters, for example from about 0.1 cubic centimeters to about 100 cubic centimeters. Thus, a diagnostically effective amount of a contrast agent used in the practice of the invention methods is much smaller than is used for other types of diagnostic techniques involving the use of contrast agents for imaging of arteries, and the like.

The term "subject" as used herein is specifically contemplated to include all mammals subject to formation of vulnerable plaques, such as domesticated pets, farm animals and zoo animals, as well as humans.

In another embodiment according to the present invention, there are provided in vivo methods for detection of vulnerable plaque(s) in a subject in need thereof using a macrophage-avid agent. In this embodiment, the invention diagnostic method comprises administering to the subject a diagnostically effective amount of a biologically compatible detectable macrophage-avid agent so as to allow the detectable macrophage-avid agent to associate with macrophages at a lipid accumulation in the wall of an artery; and detecting in vivo the presence of the detectable macrophage-avid agent attached to the macrophages at the lipid accumulation in the wall of the artery, wherein the detecting is evidence of the presence of a vulnerable plaque. Preferably the macrophage-avid agent comprises a lipid-avid agent, as described herein attached to a detectably labeled macrophage specific antibody, or fragment thereof.

Antibodies used in invention assay(s) can be polyclonal, monoclonal, or a functionally active fragment thereof. For example, antibodies to SR-BI (or CD36 antigen), a cell surface receptor expressed specifically on the macrophage cell surface to bind HLDL or LDL or oxidized LDL, are known (See U.S. Pat. No. 5,925,333, which is incorporated herein by reference in its entirety). Such antibodies are also commercially available (Pharmingen (Beckton-Dickinson), Lincoln Park, N.J.). It is believed that the collagenous domains of these macrophage scavenger receptors (SR-BI) mediate their binding specificities for polyanionic ligands (Acton, et al., *J. Biol. Chem.* 268:3530–3537, 1993). Methods for preparation of detectably labeled antibodies are also well known. See, for example, U.S. Pat. No. 4,867,973.

In general, mono- or poly-clonal antibodies are raised in appropriate host animals by immunization with immunogens using conventional techniques, or by primatizing, humanizing or genetic engineering techniques as are know in the art. The preparation of monoclonal antibodies is disclosed, for example, by Kohler and Milstein, *Nature* 256:495–7, 1975; and Harlow et al., in: *Antibodies: a Laboratory Manual,* page 726 (Cold Spring Harbor Pub., 1988), which are hereby incorporated by reference. Briefly, monoclonal antibodies can be obtained by injecting mice, or other small mammals, such as rabbits, with a composition comprising a immunogenic polypeptide or conjugate containing such a polypeptide, verifying the presence of antibody production by removing a serum sample, removing the spleen to obtain B lymphocytes, fusing the B lymphocytes with myeloma cells to produce hybridomas, cloning the hybridomas, selecting positive clones that produce antibodies to the antigen, and isolating the antibodies from the hybridoma cultures. Monoclonal antibodies can be isolated and purified from hybridoma cultures by a variety of well-established techniques. Such isolation techniques include affinity chromatography with Protein-A Sepharose, size-exclusion chromatography, and ion-exchange chromatography. See, for example, Barnes et al., Purification of Immunoglobulin G (IgG), in: *Methods in Mol. Biol.,* 10: 79–104, 1992). Antibodies of the present invention may also be derived from subhuman primate antibodies. General techniques for raising antibodies in baboons can be found, for example, in Goldenberg et al., International Patent Publication WO 91/11465 (1991) and Losman et al., *Int. J. Cancer,* 46:310–314, 1990.

It is also possible to use anti-idiotype technology to produce monoclonal antibodies which mimic an epitope. For example, an anti-idiotypic monoclonal antibody made to a first monoclonal antibody will have a binding domain in the hypervariable region which is the "image" of the epitope bound by the first monoclonal antibody.

The term "antibody" as used in this invention includes intact molecules as well as flnctional fragments thereof, such as Fab, F(ab')$_2$, and Fv that are capable of binding to macrophages. These functional antibody fragments are defined as follows:

(1) Fab, the fragment which contains a monovalent antigen-binding fragment of an antibody molecule, can be produced by digestion of whole antibody with the enzyme papain to yield an intact light chain and a portion of one heavy chain;

(2) Fab', the fragment of an antibody molecule that can be obtained by treating whole antibody with pepsin, followed by reduction, to yield an intact light chain and a portion of the heavy chain; two Fab' fragments are obtained per antibody molecule;

(3) (Fab')$_2$, the fragment of the antibody that can be obtained by treating whole antibody with the enzyme pepsin without subsequent reduction; F(ab')$_2$ is a dimer of two Fab' fragments held together by two disulfide bonds;

(4) Fv, defined as a genetically engineered fragment containing the variable region of the light chain and the variable region of the heavy chain expressed as two chains; and (5) Single chain antibody ("SCA"), a genetically engineered molecule containing the variable region of the light chain and the variable region of the heavy chain, linked by a suitable polypeptide linker as a genetically fused single chain molecule.

Methods of making these fragments are known in the art. (See for example, Harlow and Lane, *Antibodies: A Laboratory Manual,* Cold Spring Harbor Laboratory, New York, 1988, incorporated herein by reference). As used in this invention, the term "epitope" means any antigenic determinant on an antigen to which the paratope of an antibody binds. Epitopic determinants usually consist of chemically active surface groupings of molecules such as amino acids or carbohydrate side chains and usually have specific three dimensional structural characteristics, as well as specific charge characteristics.

Antibody fragments according to the present invention can be prepared by proteolytic hydrolysis of the antibody or by expression in *E. coli* or mammalian cells (e.g. Chinese hamster ovary cell culture or other protein expression systems) of DNA encoding the fragment.

Antibody fragments can be obtained by pepsin or papain digestion of whole antibodies by conventional methods. For example, antibody fragments can be produced by enzymatic cleavage of antibodies with pepsin to provide a 5S fragment denoted F(ab')$_2$. This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using pepsin produces two monovalent Fab' fragments and an Fc fragment directly. These methods are described, for example, by Goldenberg, U.S. Pat. Nos. 4,036,945 and 4,331,647, and references contained therein, which patents are hereby incorporated by reference in their entirety. See also Porter, R. R., *Biochem. J.,* 73: 119–126, 1959. Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody.

Fv fragments comprise an association of $V_H$ and $V_L$ chains. This association may be noncovalent, as described in Inbar et al., *Proc. Nat'l Acad. Sci. USA* 69:2659–62, 1972. Alternatively, the variable chains can be linked by an intermolecular disulfide bond or cross-linked by chemicals such as glutaraldehyde. Preferably, the Fv fragments comprise $V_H$ and $V_L$ chains connected by a peptide linker. These single-chain antigen binding proteins (sFv) are prepared by constructing a structural gene comprising DNA sequences encoding the $V_H$ and $V_L$ domains connected by an oligonucleotide. The structural gene is inserted into an expression vector, which is subsequently introduced into a host cell such as *E. coli*. The recombinant host cells synthesize a single polypeptide chain with a linker peptide bridging the two V domains. Methods for producing sFvs are described, for example, by Whitlow and Filpula, *Methods,* 2: 97–105, 1991; Bird et al., *Science* 242:423–426, 1988; Pack et al., *Bio/Technology* 11:1271–77, 1993; and Ladner et al., U.S. Pat. No. 4,946,778, which is hereby incorporated by reference in its entirety.

Another form of an antibody fragment is a peptide coding for a single complementarity-determining region (CDR). CDR peptides ("minimal recognition units") can be obtained by constructing genes encoding the CDR of an antibody of interest. Such genes are prepared, for example, by using the polymerase chain reaction to synthesize the variable region from RNA of antibody-producing cells. See, for example, Larrick and Fry, *Methods,* 2: 106–10, 1991.

Methods for attaching one or more detectable-labels to an antibody are well known in the art and are illustrated in the Examples herein.

For in vivo diagnosis, any biologically compatible detectable lipid-avid agent, lipid-avid agent labeled with a biologically compatible detectable label known in the art, or detectably labeled macrophage-avid agent can be used in the practice of the invention methods so long as the detectable lipid-avid agent, detectably labeled lipid-avid agent, or detectably labeled macrophage-avid agent can be detected by a desired non-invasive or invasive method. For example, in one embodiment the lipid-avid agent is a contrast agent formed by attaching to the lipid-avid agent of a biologically compatible heavy metal ion, such as barium, rhenium, thallium, bismuth, iridium, gadolinium, cesium, lanthanum, strontium, technetium, radium, indium, tantalum, gold, iron, and the like, or other ions or atoms such as iodine, or radioactive isotopes.

Such lipid-avid contrast agents or invention compounds comprising such lipid-avid contrast agents can be used in the practice of the invention methods in conjunction with detection modalities as are known in the art for use with other types of heavy metal ion contrast agents, such as magnetic resonance or x-ray fluoroscopy imaging or electron beam CT scanner (EBCT).

In an alternative embodiment, the heavy metal ion is ferromagnetic, preferably an iron ion, and the detection modality is one that detects the presence of an accumulation of the ferromagnetic ions in vulnerable plaques in the arterial wall. A preferred device for detecting a lipid-avid agent containing a ferromagnetic ion in an arterial wall is an intra-arterial catheter containing a sensor sensitive to the ferromagnetic ion, as is known in the art.

Alternatively, the detectable label attached to the lipid-avid agent or macrophage-avid agent containing such a lipid-avid agent, can be a biologically compatible radioactive substance having a half-life longer than the period required for the unbound detectable lipid-avid agent to clear from the subject, but short enough to avoid significant damage to healthy tissue in the subject. In selection of the radioactive substance, it is important to take into account that (although a portion of the detectable or detectably labeled lipid-avid agent will be excreted by natural processes) the portion of the detectable or detectably labeled lipid-avid agent that penetrates vessel walls and becomes trapped in vulnerable plaques will remain in the arterial walls for up to several weeks. Therefore, as the term is used herein, "a biologically compatible radioactive substance" is one having a half-life short enough to avoid substantial damage to the subject caused by radioactive substances trapped in lipid accumulations. For example, a radioactive substance having a half-life in the range from about 2 hours to about 96 hours can be used in practice of the invention diagnostic methods. Representative examples of such radioactive substances useful in practice of the invention method include radioactive forms of barium, rhenium, iodine, thallium, bismuth, iridium, gadolinium, cesium, lanthanum, strontium, technetium, radium, indium, tantalum, gold, iron, and the like. At present, radioactive forms of rhenium or technetium that have half-lives in the above range are preferred, as such radioactive substances are rapidly excreted in the urine without binding to tissues in the kidney or bladder and some are FDA approved for in vivo administration to humans.

In a presently preferred embodiment, when heparin or a heparin fragment is used as the lipid-avid agent, the heparin is modified by conjugation with one or more aromatic amino acids, such as phenylalanine, iodo-phenylalanine or tyrosine, or N-triiodobenzoyl-lysine, triiodobezamide conjugated with diamino aliphatic linkers (e.g., containing from about 2 to about 12 carbons) or iodinated aromatic amino acid polymers (such as poly-Iodophenylalanine, poly-tyrosine, and poly-phenylalanine), and the like, to significantly increase the lipophilicity of the molecule. Alternatively, tyrosine and 4-iodophenylalanine or the above-mentioned iodinated compounds can be used to attach covalently radioactive iodine ($^{125}I$ or $^{131}I$) to the invention lipid avid agents. Heparins, heparin fragments, and polyanion carbohydrates modified by conjugation with such lipophilicity-increasing molecules exhibit increased binding to LDL and oxidized LDL compared with unmodified molecules and are expected to show increased penetration through blood vessel walls. In addition, the lipophilicity increasing amino acids are readily utilized for attaching detectable labels to the lipid-avid agents of the invention. For example, a tyrosine can be readily iodinated to obtain a lipid-avid agent that is useful as a contrast agent. Alternatively, 4-iodophenylalanine can be used to attach a radioactive iodine to the invention lipid-avid agents. A nicotinic acid-based chelator can be used to attach certain lanthanide radioions to the lipid-avid agents. For example, a nicotinic acid-based chelator, such as succinimidyl 6-hydrazinonicotinate hydrochloride, can be used to chelate $^{99m}$Technetium to the invention lipid-avid agents to render them detectable, as disclosed in Example 5 hereinbelow.

Lipid-avid agents and macrophage-avid agents labeled with such radioactive substances and trapped in lipid pools in subjects can be detected using known detection modalities, such as scanning electron beam computed tomography, MRI, single photon emission computed tomography, and the like, as is known in the art.

Antibodies specific for macrophages are known in the art and commercially available. For instance, antibodies to the CD36 antigen, which is known to be expressed almost exclusively on macrophages, are sold by Pharmingen (San Diego, Calif.).

EBCT, also known as the ultra fast CT or cine CT, is presently preferred for detecting the invention labeled lipid-avid agent that has bound to lipid pools containing oxidized LDL in arterial walls in and near the heart. The advantage of EBCT over conventional CT scanning for cardiac imaging derives from the very rapid scan acquisition time, typically 50 msec to 100 msec. This extremely rapid acquisition time results from specific design features of the EBCT that differ from those of a conventional CT scanner.

A conventional CT scanner consists of a rotating x-ray source and a linear array of detectors. The x-ray beam emanating from the source must be rotated around the patient during data acquisition such that every point within the patient is traversed by an x-ray beam within that field of view (slice thickness). This process is quite cumbersome and is the time-limiting factor for data acquisition in routine CT scanning. Typically, scans take 1–2 seconds to complete in a conventional CT scanner. Given the rapidity of cardiac motion, conventional CT scanning is not very satisfactory for in vivo cardiac imaging due to significant artifacts resulting from such motion.

However, EBCT has reduced scan times to from about 10 milliseconds to about 0.6 sec by eliminating the movement of the x-ray source. In EBCT, a beam of electrons created by an electron gun is focused onto a focal point and then deflected by electromagnetic forces onto target rings made of tungsten. These rings form an arc, generally of 210° centered below the patient. As the electron beam is rotated around these arcs, the resultant x-rays pass through the patient in all planes and are then registered on detectors. In addition to permitting detailed cardiac imaging without artifacts created by heart motion, the rapid acquisition time of EBCT has the additional benefits of (i) minimizing patient exposure to radiation and (ii) diminishing overall scan time.

In those embodiments of the invention method wherein the detectable label is a radioactive substance, detecting can also be performed invasively, for example, using an intra-arterial catheter containing a sensor sensitive to the radioactive substance, as is known in the art.

For in vivo detection methods, the detectable or detectably-labeled lipid-avid agent or macrophage-avid agent is administered by injection into the circulatory system so that the detectable agent can be absorbed into any lipid pools in the arteries. Generally, the detectable lipid-avid agent or macrophage-avid agent containing such a lipid-avid agent is administered into the arterial tree, for example, into an artery proximal to the heart. However, the detectable lipid-avid agent, and the like, can also be administered by injection into the venous system. Any of a variety of intra-arterial or intra-venous catheters known in the art for delivery of liquids (e.g., for delivery of contrast agents and detectably labeled substances) can advantageously be used to inject the lipid-avid agent into the circulatory system.

As the heart is the area of the body in which vulnerable plaque is perhaps most deadly, it is generally advisable to focus the detection efforts on the area surrounding the subject's heart. In fact, in many cases, it may be sufficient to scan only the heart area of the subject to search for evidence that the invention detectable lipid-avid or macrophage-avid agent has been captured in or at a lipid accumulation containing oxidized LDL, signaling the presence of a vulnerable plaque.

In another embodiment according to the present invention, there are provided method(s) for obtaining an animal model of a vulnerable plaque. The invention method for obtaining a vulnerable plaque animal model comprises locally depositing a plaque-forming amount of a lipid containing oxidized LDL into one or more blood vessel walls of a live pig while minimizing thrombogenesis so as to form one or more lipid accumulations in the vessel walls, and allowing the bodily processes of the live pig to react to the lipid accumulations to form one or more structures found in a human vulnerable plaque.

The term "a plaque-forming amount" of a lipid deposited according to the invention method means the amount of lipid necessary to cause one or more structures to form at or near the site of the local deposition that characterize a human vulnerable plaque. For example, the amount of lipid deposited is generally a single bolus of from about 0.3 ml to about 2.0 ml of the lipid per injection site. It is presently preferred that the lipid contains a concentration of up to 75% by volume of oxidized LDL and is deposited directly into one or more coronary arteries of a live pig while minimizing thrombogenesis so as to form one or more lipid accumulations in the vessel walls. The bodily processes of the live pig will react to the lipid accumulations so as to form one or more of the structures that characterize a vulnerable plaque in a human, for example, within about 28 days to about 3 months. Preferably the lipid is locally deposited into the tunica media of one or both coronary arteries of the pig, for example, by means of an intramural delivery catheter.

Optionally, the lipid containing oxidized LDL can be administered encapsulated in a coacervate, such as a olive oil/albumin coacervate, to create a less viscous fluid for injection. For example, a coacervate of microcapsules no larger than about $100\mu$ can be formed for convenient injection via an IVT catheter.

The porcine model of a vulnerable plaque produced by the invention method is characterized by one or more of the following indications at the site of the lipid accumulations: neointimal hyperplasia, medial necrosis, recruitment of macrophages and/or lymphocytes, formation of giant cells, and rupture of the vessel with accompanying clot formation and is useful for studying the characteristics of vulnerable plaque in humans and for developing treatment modalities therefor.

To mimic in the model the formation of foamy cells and local inflammation in vessel walls found in the vicinity of vulnerable plaques of subjects, the lipid containing oxidized-LDL can be deposited in conjunction with one or more of the following: pre-cultured and stimulated monocytes, stimulated CD-4 lymphocytes in cell suspension, granulocyte-macrophage colony stimulating factor (GMCF), additional cytokines (e.g. interleukin-1 or interleukin 8), vascular cell adhesion molecule (VCAM-1), monocyte chemoattractant protein (MCP-1), granulocyte-macrophage colony stimulating factor (GMCF), and the like.

For injection of lipids (or oxidized lipids) or lipids in conjunction with monocyte/lymphocyte cell suspension, cytokines or other biological agent into the wall of the arterial tree in preparation of the animal model, consistent and circumferential deposition of the detectable lipid-avid agent, without substantial systemic washout and/or vessel wall damage, is preferred. Generally, an injection catheter is used to accomplish injection, and the preferred catheter for this purpose is currently the Infiltrator Local Drug Delivery™ balloon catheter (IVT, Inc., California), which has been developed specifically to meet the demands of direct intramural drug deposition.

The invention in vivo diagnostic methods are useful for determining those individuals with a vulnerable plaque, which, if ruptured, would increase the probability of forming an occluding thrombus in an artery. In addition, the invention diagnostic methods are useful for determining the location of such a vulnerable plaque so that its size, development, and the like, can be monitored or so that treatment can be undertaken.

In addition, since pools of lipids in arterial walls are associated with sites of inflammation, the invention methods are useful for detecting sites of inflammation in arterial walls associated with such pools of lipids. Thus, the invention methods are used for determining those individuals with a heightened probability of heart attack or stroke, especially of a fatal or near fatal heart attack or stroke.

The invention animal model of a vulnerable plaque is useful for laboratory study of the properties of vulnerable plaque in humans and for studying in vivo methods for detection of vulnerable plaque (i.e. in the animal model or in humans). In addition, the invention animal model of a vulnerable plaque is useful for creating arterial sections containing vulnerable plaques that can be used to perform in vitro assays for testing various putative detectably labeled lipid-avid agents for use in the invention in vivo diagnostic methods.

The invention will now be described in greater detail by reference to the following non-limiting examples.

EXAMPLE 1

Studies were performed to develop a reproducible technique for the introduction of lipid into the arterial wall of pigs to serve as an animal model for vulnerable plaque. The pig model was chosen as the experimental species based on the large extent of prior experience with this model. Additionally, in pigs the coronary artery size and anatomy are similar to those in humans.

Refined pig lard and olive oil (in place of oxidized-LDL) were used as the source of lipid. These lipids are very inexpensive, have very high cholesterol content, and are readily available. The lard was liquefied by heat and then injected as a 0.5 ml single bolus injection into the carotid arteries of several pigs. Pigs used in the studies were housed in facilities and handled prior to and during the study according to methods that conform to the guidelines set forth by the National Institute of Health, the Animal Welfare Act, and the American Association for the Accreditation of Laboratory Animal Care.

The treated pigs were sacrificed at various times (less than 1 day) after the injection by administration of a barbiturate overdose via an ear vein (Sleepaway™ 12 mls). This method of euthanasia is consistent with the recommendations of the Panel of Euthanasia of the American Veterinary Medical Association. Post sacrifice, arterial segments were removed for histological analysis.

The histological samples of treated pig arteries were prepared by sectioning at necropsy and freezing at −70° C. Arterial samples subsequently were cut using a microtome and mounted on a coverslip. Standard Hemotoxylin and Eosin (H+E) stain and an Oil Red 0 stain were performed. The latter resulted in simple lipids staining red, and cell nuclei staining blue. This study showed the feasibility of depositing larger quantities of lipid in the arterial wall.

EXAMPLE 2

Preparation of Iodine Labeled Heparin Fragments

In a further study, iodine was covalently bound to phenylalanine and conjugated to heparin. More highly iodinated compounds like N-triiodobenzoyl lysine methyl ester or triodobenzamide can also be conjugated to heparin as well. High levels of iodine-containing amino acids conjugated to heparin facilitate visualization by EBCT scanning of the lipids injected into an arterial wall in the pig model.

Oxidized-LDL was prepared in standard fashion and supplied by the laboratory of Dr. Luigi Spagnoli in Rome, Italy. This lab has substantial expertise in lipids.

The oxidized-LDL, which is used to simulate a pooling of lipids in a vulnerable plaque, was injected directly into the tunica media of the carotid artery of a group of pigs in varying amounts in the range from 0.1 ml to 3 ml using a specialized 27G needle and a small syringe (standard "TB syringe). Then the animals were returned to quarters for various periods of time. This process was well tolerated and in experienced hands is easily reproducible. No arteriotomy was necessary and, therefore, the degree of thrombus is minimal.

Labeled low molecular weight heparin in amounts varying from 5 cc to 200 cc was administered intravenously to the test animals that have been treated with lipid injections, a period of from 2 hrs to 24 hours was allowed to pass in which the detectable lipid-avid agent was allowed to penetrate arterial walls in the test animals and bind to injected oxidized-LDL while unbound heparin was excreted. Then the pigs were sacrificed and arterial sections were prepared as described above in Example 1.

The sections were subjected to electron beam CT scanner (EBCT) with a very rapid scan acquisition time of 50 msec to 100 msec to detect labeled heparin, which was bound to macroscopic accumulations of oxidized LDL in the walls of the carotid artery.

EXAMPLE 3

Subsequent to success of the test described in Example 2, delivery of oxidized-LDL to the coronary circulation of pigs was performed using an endovascular catheter designed for mural local drug delivery (Infiltrator Local Drug Delivery™ balloon catheter, IVT, Inc., California). The oxidized LDL used in this experiment was an olive oil/albumin coacervate prepared using a known procedure and having a microparticle size of about 100µ having an oxidized LDL concentration of about 75% by volume as well as proinflammatory properties.

In this study, a total of 21 coronary arteries (10 pigs) were injected with 0.5 ml of the coacervate. The survival time for each animal post injection varied from 2 hours to 28 days.

Figure 1:
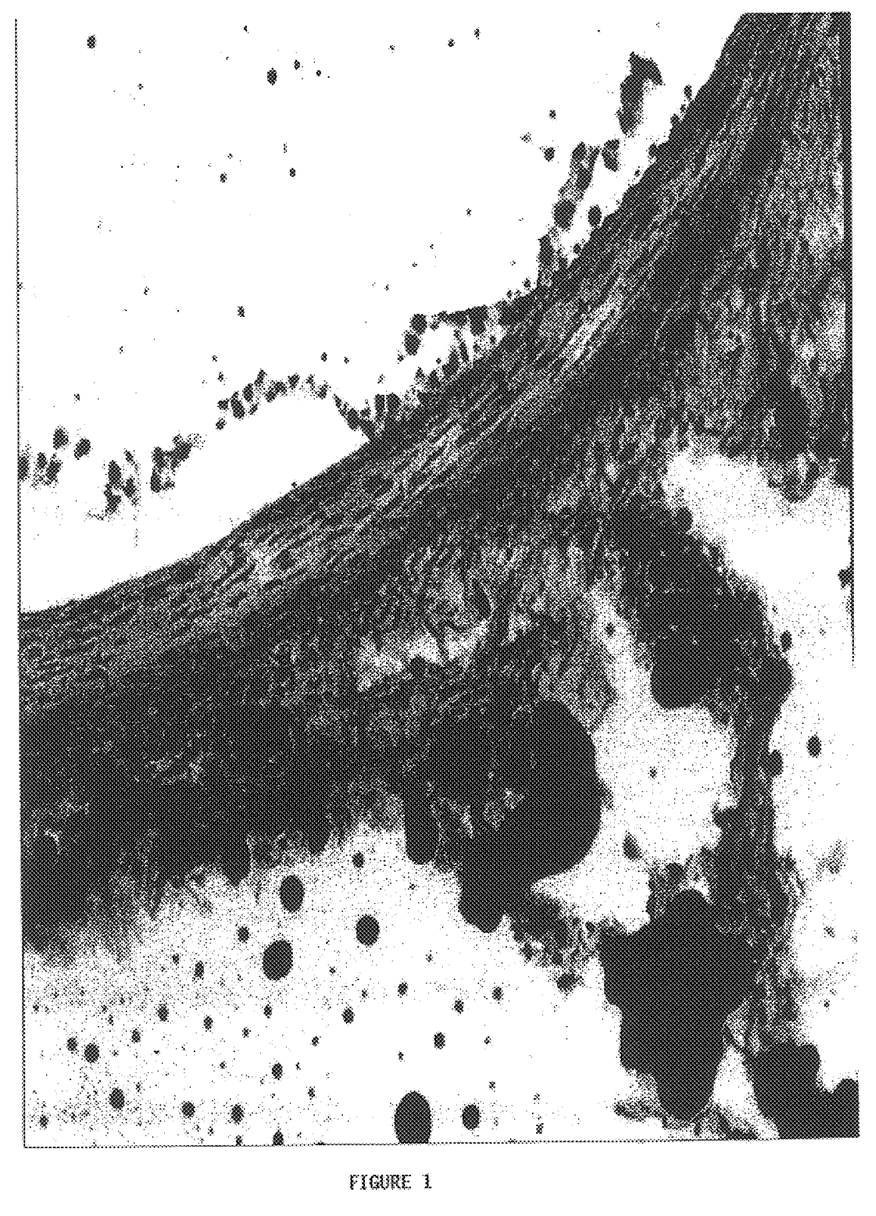
FIG. 1 is a color photograph of a histological sample of pig artery stained with oil Red 0 stain showing the presence of substantial subintimal lipid accumulations (in red). Macrophages colonized in the deposits are stained in blue.
Figure 2:
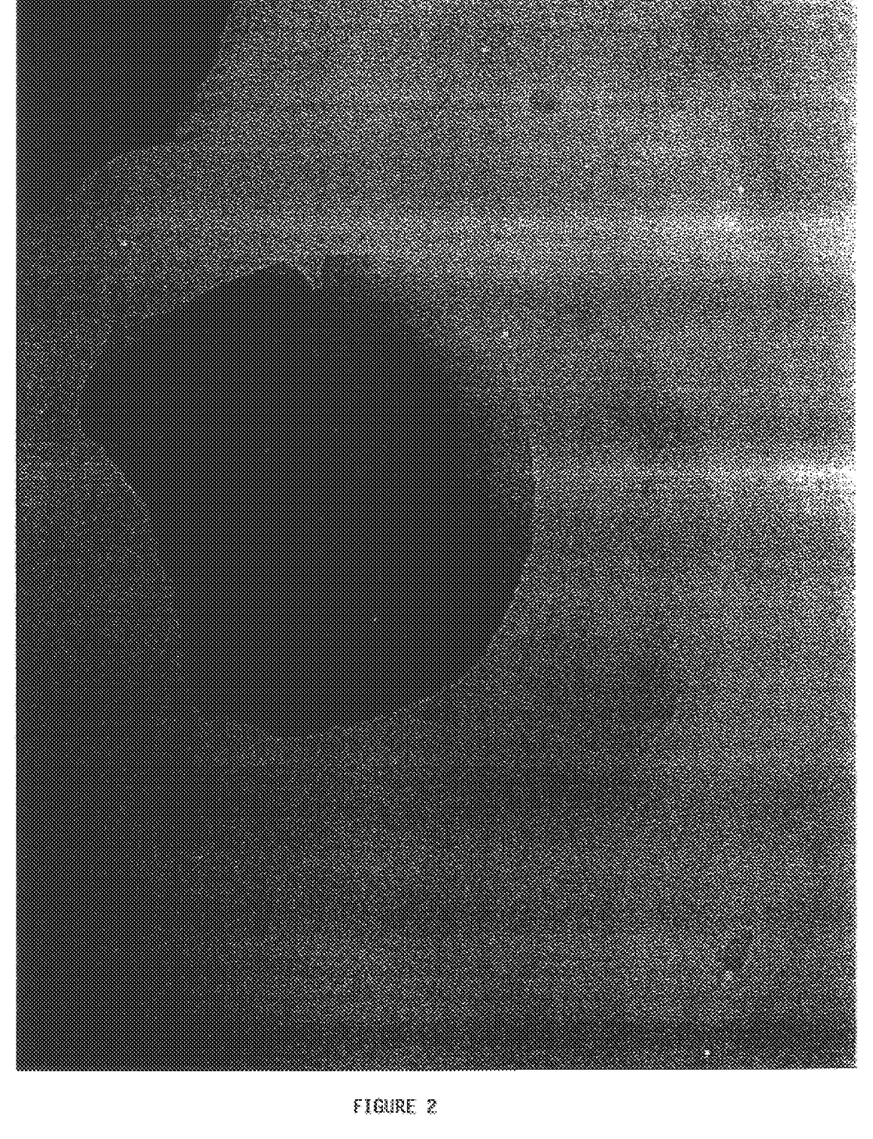
FIG. 2 is a color photograph showing a cross section of pig artery with lipid accumulation (in yellow).
Figure 3:
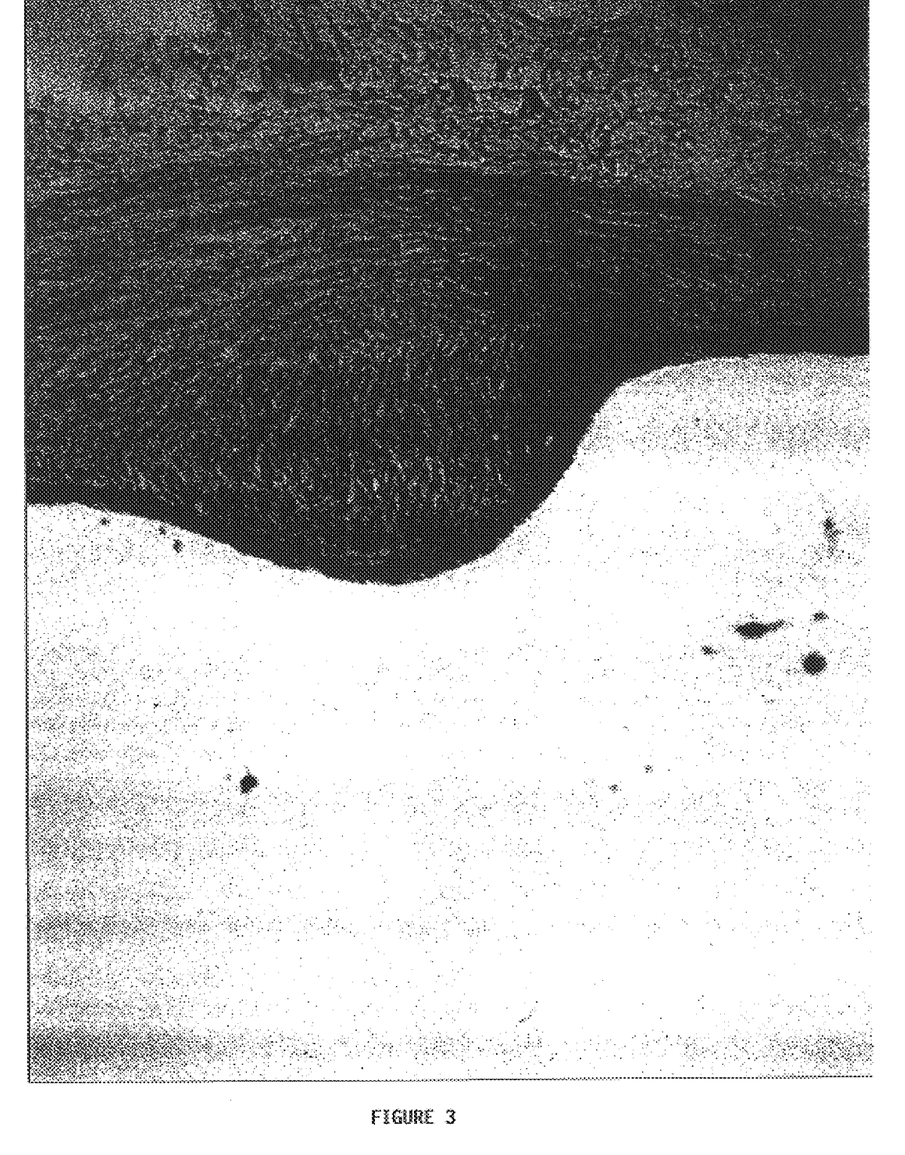
FIG. 3 is a color photograph of a histological sample of pig artery showing substantial neointimal hyperplasia at the site of lipid injection.

The lipid were still evident 28 days following treatment (shown in FIG. 2). In arteries treated 14 days or longer prior to sacrifice, macrophages had colonized these deposits and contained intracellular lipid as determined by specialized immunostains (i.e. HAM 56). Histological samples prepared with oil Red 0 stain confirmed the presence of substantial subintimal lipid accumulations (FIGS. 1 and 2). On routine (H+E) histological analysis, a degree of neointimal hyperplasia (FIG. 3) and medial necrosis was detected at treatment sites.

These histological procedures revealed a mild inflammatory response in the region of the injected lipids as shown by the recruitment of macrophages/lymphocytes to the site of injected lipids, formation of giant cells, and the presence of intracellular lipid. In addition, there was substantial neointimal hyperplasia (FIG. 3) at the site of injection, with the extent of neointimal hyperplasia correlating with the degree of treatment-induced vessel wall injury.

Figure 4:
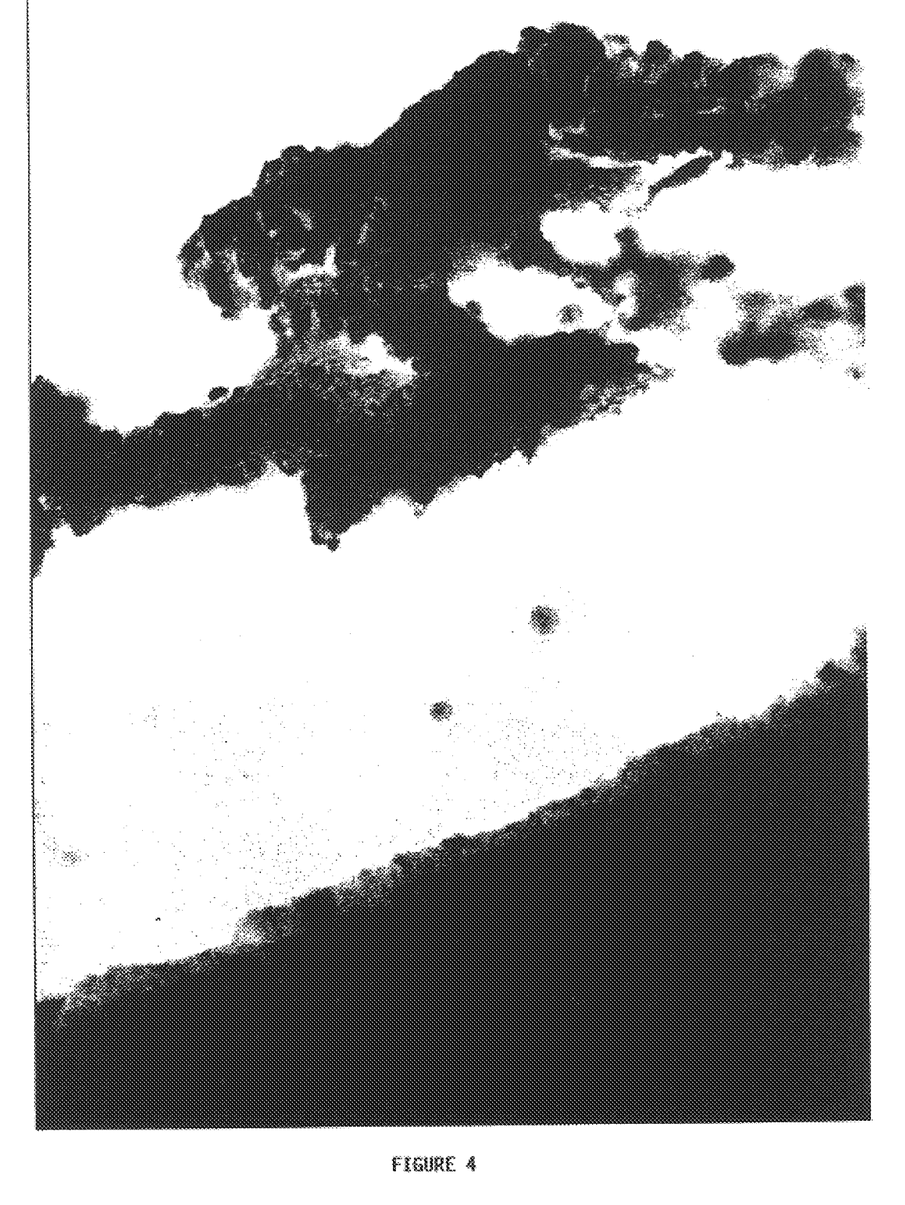
FIG. 4 is a color photograph of a histological sample of pig artery showing plaque rupture in the artery wall and accompanying thrombus.

Surprisingly, one of the pigs suffered a sudden death 13 days after injection of the high ox-LDL coacervate into a coronary artery. Post mortem examination revealed that the pig had undergone a plaque rupture and hemorrhage at the site of injection, as shown in FIG. 4. Acute thrombus was also present at the site of rupture. An arterial cross section of the coronary artery of the pig that suffered sudden death showed extensive neointimal formation around the lipid pool in the side of the artery.

In addition, a technique of immunocytochemistry using one of the many commercially available antibodies to oxidized-LDL was utilized to confirm successful lipid delivery, and the extent of calcification present was evaluated by staining with van Fossa stain. These results show that injection of ox-LDL into porcine arteries is a valid animal model for study of the invention treatment methods.

EXAMPLE 4

Administration of the Labeled Heparin Fragments

Amounts of the labeled low molecular weight heparin in the range from 5 cc to 200 cc were injected into the arterial walls of pigs and allowed to penetrate arterial walls and attach to lipid accumulations in the arterial walls. Macrophage colony stimulating factor (GMCF) was added to the injectate to excite an macrophage intensive inflammatory reaction in an effort to reproduce the known characteristics of a vulnerable atherosclerotic plaque. The degree of luminal compromise for each pig was assessed by angiography to establish the presence of some luminal stenosis.

Serial EBCT scans were performed before and after injection of varying concentrations of the detectable lipid-avid agent into the arterial wall. The ability of the EBCT scanner to detect microliter quantities of contrast agent was thus gauged.

Post mortem histological analysis was used as a control to confirm the sensitivity of the assay by determining whether areas deemed positive for the labeled heparin on the EBCT images correspond to arterial segments into which the lipid was injected, and for specificity by determining whether areas deemed negative correspond to "virginal" arterial segments.

EXAMPLE 5

Preparation of Phenylalanine-Hydrazinonicotinamide Heparin Conjugate

A heparin/phenylalanine conjugate was prepared to increase the lipophilicity of heparin in anticipation of increased binding to LDL or oxidized LDL. A second modification to "visualize" the binding in vivo was incorporated by doping the phenylalanine methyl ester reactant with 1,6-diaminohexane during its conjugation to heparin. The incorporated amino groups were modified with succinimidyl hydrazinonicotinate hydrochloride (SHNH) to ultimately incorporate hydrazinonicotinamide moieties. This moiety chelates $^{99m}$Technetium, the meta stable form of $^{99}$Technetium.

In vitro tests have shown that conjugation of an aromatic amino acid with heparin in this manner significantly increased the lipophilicity and binding affinity to LDL and oxidized LDL of the conjugate compared with unmodified heparin.

It will be apparent to those skilled in the art that various changes may be made in the invention without departing from the spirit and scope thereof, and therefore, the invention encompasses embodiments in addition to those specifically disclosed in the specification.

That which is claimed is:

1. A method for obtaining an animal model of a vulnerable plaque, said method comprising:

locally delivering a lipid containing oxidized LDL directly into one or more blood vessel walls of a live pig while minimizing thrombogenesis so as to form one or more lipid accumulations in the vessel walls, and allowing the bodily processes of the live pig to react to the lipid accumulations to form one or more structures selected from the group consisting of an accumulation of oxidized low density lipoproteins, a presence of metalloproteinases, local inflammation, inflammatory cell activity, a presence of a collagen cap or fibrous scar, and thrombus found in a human vulnerable plaque.

2. The method according to claim 1 wherein the lipid is delivered into the tunica media of one or both coronary arteries of the pig.

3. The method according to claim 1 wherein the lipid is delivered by means of an intramural delivery catheter.

4. The method according to claim 1 wherein the lipid is contained within an olive oil/albumin coacervate.

5. The method according to claim 1, wherein the method further comprises delivery with the lipid of one or more of the following:

pre-cultured and stimulated monocytes, stimulated CD-4 lymphocytes in cell suspension, granulocyte-macrophage colony stimulating factor (GMCF), vascular cell adhesion molecule (VCAM-1), monocyte chemoattractant protein (MCP-1), granulocyte-macrophage colony stimulating factor (GMCF), interleukin-1 or interleukin 8, whereby foamy cells and local inflammation are produced adjacent to the lipid accumulations in the vessel walls.

6. The method according to claim 1 wherein the pig is allowed to react to the lipid accumulations for about 28 days to about 3 months.

7. The method according to claim 6 wherein the structures formed are selected from the group consisting of neointimal hyperplasia, medial necrosis, recruitment of macrophages and/or lymphocytes, formation of giant cells, and rupture of the vessel with accompanying clot formation.

8. A porcine model of a vulnerable plaque produced by the method of claim 1.

* * * * *

(12) EX PARTE REEXAMINATION CERTIFICATE (5706th)
United States Patent
Teirstein et al.

(10) Number: US 6,580,016 C1
(45) Certificate Issued: Mar. 13, 2007

(54) ANIMAL MODEL FOR DETECTION OF VULNERABLE PLAQUES

(75) Inventors: Paul S. Teirstein, La Jolla, CA (US); Kenneth W. Carpenter, Del Mar, CA (US); Istvan Szinai, San Diego, CA (US); David A. Schwartz, Encinitas, CA (US)

(73) Assignee: Medivas, L.L.C., La Jolla, CA (US)

Reexamination Request:
No. 90/006,931, Feb. 12, 2004

Reexamination Certificate for:
Patent No.: 6,580,016
Issued: Jun. 17, 2003
Appl. No.: 09/760,182
Filed: Jan. 12, 2001

Related U.S. Application Data

(62) Division of application No. 09/453,668, filed on Dec. 3, 1999, now abandoned
(60) Provisional application No. 60/111,084, filed on Dec. 4, 1998.

(51) Int. Cl.
*A01K 67/00* (2006.01)
*A01K 67/033* (2006.01)

(52) U.S. Cl. ............................................. 800/9; 424/9.1
(58) Field of Classification Search ..................... 800/9, 800/10, 11, 12; 424/9.1, 9.2, 1.11
See application file for complete search history.

(56) References Cited

U.S. PATENT DOCUMENTS 4,963,367 A * 10/1990 Ecanow ...................... 424/485

OTHER PUBLICATIONS

Calara et al. Arterioscler. Thromb. Vasc. Biol., 18:884–893 (Jun. 1998).*
Barath et al. Catherization and Cardiovascular Diagnosis, 41:333–341 (1997).*
Biwa et al. The Journ. Of Biol. Chem., 273(43):28305–28313 (Oct. 23, 1998).*
Schwartz et al., The Pathogenesis of Atherosclerosis, Clinical Cardiology, vol. 14, No. 1, pp. 1–16, (1991).
Reitman et al., Yucatan Miniature Swine as a Model for Diet–Induced Atherosclerosis, Atherosclerosis, vol. 43, pp. 119–132, (1982).
Bell et al., Evidence for an Altered Lipid Metabolic State in Cicrculating Blood Monocytes Under Conditions of Hyperlipemia in Swine & Its Implications in Arterial Lipid Metabolism, Arteriosclerosis & Thrombosis, vol. 12, No. 2, pp. 155–162, (1992).

* cited by examiner

*Primary Examiner*—Plam R. Shukla (57) ABSTRACT

The present invention provides in vivo methods for detection of vulnerable plaque in a subject in need thereof. In the invention method the subject is administered a diagnostic amount of a biologically compatible detectable lipid-avid agent, the detectable lipid-avid agent is allowed to penetrate arterial walls and attach to any lipid accumulations of oxidized LDL-cholesterol in arterial walls in the wall of an artery; unbound detectable lipid-avid agent is allowed to clear from the body by natural processes, and the presence of the detectable lipid-avid agent attached to the lipid accumulation in the wall of the artery is detected. Detection of bound lipid-avid agent indicates the presence of a vulnerable plaque and predicts a heightened risk of lethal heart attack or thrombus. The detectable lipid-avid agent is selected for its ability to penetrate arterial walls and bind with oxidized LDL-cholesterol in the lipid accumulation in a vulnerable plaque. Alternatively, macrophage-avid agents, for example a lipid-avid agent attached to a macrophage-specific antibody, can be used in the invention methods. The invention further includes methods for in vitro assays for detecting vulnerable plaque and a porcine animal model of vulnerable plaque useful for testing treatment modalities.

EX PARTE REEXAMINATION CERTIFICATE ISSUED UNDER 35 U.S.C. 307

THE PATENT IS HEREBY AMENDED AS INDICATED BELOW.

AS A RESULT OF REEXAMINATION, IT HAS BEEN DETERMINED THAT:

Claims 1–8 are cancelled.

* * * * *